United States Patent [19]
Fishman et al.

[11] Patent Number: 5,044,356
[45] Date of Patent: Sep. 3, 1991

[54] APPLICATOR AND GUM MASSAGING DEVICE

[76] Inventors: John Fishman, 7972 Biscayne Point Cir., Miami Beach, Fla. 33141; Iris Lopez, 750 SW. 10 St., Miami, Fla. 33130

[21] Appl. No.: 563,691

[22] Filed: Aug. 6, 1990

[51] Int. Cl.⁵ ............... A61H 9/00; A61G 17/02
[52] U.S. Cl. .................... 128/62 A; 433/80
[58] Field of Search ............... 128/62 A; 433/80, 166

[56] References Cited

U.S. PATENT DOCUMENTS

| | | | |
|---|---|---|---|
| 781,292 | 1/1905 | Murphree | 128/62 A |
| 2,788,000 | 4/1957 | Lather et al. | 128/62 |
| 3,624,908 | 1/1970 | Rickets et al. | 433/118 |
| 3,675,645 | 7/1972 | Samiran et al. | 128/62 A |
| 3,967,617 | 7/1976 | Krolik | 128/36 |
| 3,972,122 | 8/1976 | Sutter | 433/118 |
| 4,014,354 | 3/1977 | Garrett | 132/90 |
| 4,156,620 | 5/1979 | Clemens | 134/6 |
| 4,173,828 | 11/1979 | Lustig et al. | 433/87 |
| 4,347,839 | 9/1982 | Youngclaus, Jr. | 128/62 A |
| 4,576,190 | 3/1986 | Youssef | 132/89 |
| 4,605,025 | 8/1986 | McSpadden | 132/92 R |
| 4,628,564 | 12/1986 | Youssef | 15/167 R |
| 4,880,382 | 11/1989 | Moret et al. | 433/118 |
| 4,909,241 | 3/1990 | Burn et al. | 128/62 A |

*Primary Examiner*—John J. Wilson
*Assistant Examiner*—Cindy A. Cherichetti
*Attorney, Agent, or Firm*—Malloy, Downey & Malloy

[57] ABSTRACT

A handheld gum massaging device of the type which includes a wand with a movable distal dip zone and a handle connected to the wand which includes means to move the distal tip zone of the wand in a massaging action. The distal tip zone carries an element of absorbent material for receiving and applying a charge of medicament so that when the wand tip zone is moving, the element not only massages the gums but, simultaneously, delivers the medicament topically to the gums.

2 Claims, 1 Drawing Sheet

APPLICATOR AND GUM MASSAGING DEVICE

BACKGROUND OF THE INVENTION

1. Field of the Invention

This invention relates to a handheld dental tool for massaging the gums of a user and which includes a distal tip zone carrying a charge of medicament to be applied to the gums during the massaging operation.

2. Background and Description of Some Prior Art

In the past, it has been recognized that it is beneficial for the gum tissues to be massaged in order to assist in the treatment of gingivital or periodontal conditions. Massage of the gums in recommended when such conditions persist, and there have been numerous dental tools in the past for the purpose of applying massaging vibratory motion to the gum tissue. Representative prior art is set forth hereinafter but, generally, it is known to provide a handle which serves as a housing for a motor and rechargeable batteries electrically interconnected in a circuit which includes an on/off switch and which is adapted to drive a motor carried within a housing to move a power-driven socket or wand. This invention utilizes such a combination for the purpose of moving a tip which is of absorbent material so that, in addition to the massaging function known in the prior art, there is, also, an application topically of medicament carried by the absorbent tip.

U.S. Pat. No. 3,624,908 is of a dental tool which imparts a reciprocating movement to a extending portion which, through electrical power, can be utilized to manipulate an abrasive strip or, indeed, be used as a saw.

U.S. Pat. No. 3,967,617 is of a gum massaging device in which in element is caused to move in a predetermined path at the tip for the purpose of massaging.

U.S. Pat. No. 3,972,122 is of a dental instrument to cause a piston to move for cutting operations.

U.S. Pat. No. 4,156,620 is of a device wherein a tuft of filaments is rotated in a predetermined, controlled and reciprocating manner. This patent discusses the prior art which falls into three broad categories. First, non-powered brushes. Second, powered brushes, which move in a rotary, arcuate, reciprocating or orbital path driven by a power mechanism. Third, a brush head which is substantially stationary and with respect to which individual tufts are mechanically rotated either uni-directionally or, as in the case of U.S. Pat. No. 4,156,620, in a clockwise and then a counterclockwise motion.

U.S Pat. No. 4,347,839, is of a gum massaging device which includes a wand with a tip, the wand being driven by a shaft which is energized by a power source composed of batteries housed in a handle with the handle being interconnected to the wand so that when the motor is energized, movement is imparted to the wand and its tip.

U.S. Pat. No., 4,576,190, is of a dental appliance which utilizes a shaft which may be employed for various functions, such as brushing, picking, flossing, etc.

U.S. Pat. No. 4,605,025, is of a dental flossing device wherein means are provided for imparting osciloatory motion to the floss which is characterized by a mechanical clutch which is responsive to force applied against the floss to engage the floss holder With the power element to begin osciloation of the floss.

SUMMARY OF THE PRESENT INVENTION

This invention is, generally, one which utilizes a conventional handheld dental tool composed of a movable wand and a handle which is structured to house a battery power source. The batteries may be rechargeable, and in any event are included in a circuit with an on/off switch and a means to move the wand. The present invention includes a tip for the wand which is of absorbent material, and is, therefore, adapted to carry medicaments so that as the wand moves, the tip in addition to massaging the gums applies medicine thereto.

The purpose of this device is to produce a stimulating effect upon the gum tissues and to apply medicament thereto by carrying chemo-therapeutic solutions to the gingival structures. The wand tip of the present invention is replaceable and is composed of an absorbent, yet firm material. In use, a stimulating action is produced by a massaging effect when the tip is electrically energized. There are various types of motions which may be imparted to the tip, rotary, reciprocable, orbital, etc.; however, the action is to massage and stimulate the papillary areas, as well as to stimulate the marginal-cervical areas of the gum tissues and, additionally, to carry medicaments to the massaged area. Preferably, the tip is of conical or frusto-conical shape and is composed of a hard, yet an absorbent surface to allow the application of medicament solutions to the sucular areas where either initial gingivitis conditions prevail or where more advanced periodontal conditions prevail. In a preferred embodiment, the wand of the present device is bendable to adapt it to reach different locations, some of which are ordinarily difficult to anticipate in the construction of the device initially. The adaptability provided by a bendable shaft permit the user to configure the wand so that for the user's particular condition, the tip provides the desired massaging effect at the correct location while simultaneously delivering the medicament.

Generally speaking, this invention is, therefore, of an electrically energized, stimulating and massaging device for the gum tissues, specifically the interdental papillai, which is also capable of delivering medicament to the massaged zone. When used with other oral hygiene devices, such as toothbrushing and flossing, the overall oral hygiene of a user is enhanced in that the gums are adapted to be massaged with the device and, simultaneously, medicament delivered to an area requiring treatment.

In accordance with the foregoing summary of this invention, and in view of the description which follows hereinafter, reference will now be made to the accompanying drawings, in which:

DETAILED DESCRIPTION OF THE PREFERRED EMBODIMENT

In the prior art, there are numerous handheld devices which include a handle housing a battery power source and a wand connected to the handle through a means which causes the distal end of the wand to move, either in a reciprocating, isolating or vibratory manner. Representative prior art patents in the field are 2,788,000; 3,624,908; 3,967,617; 4,014,354; and 4,576,190.

Figure 1:
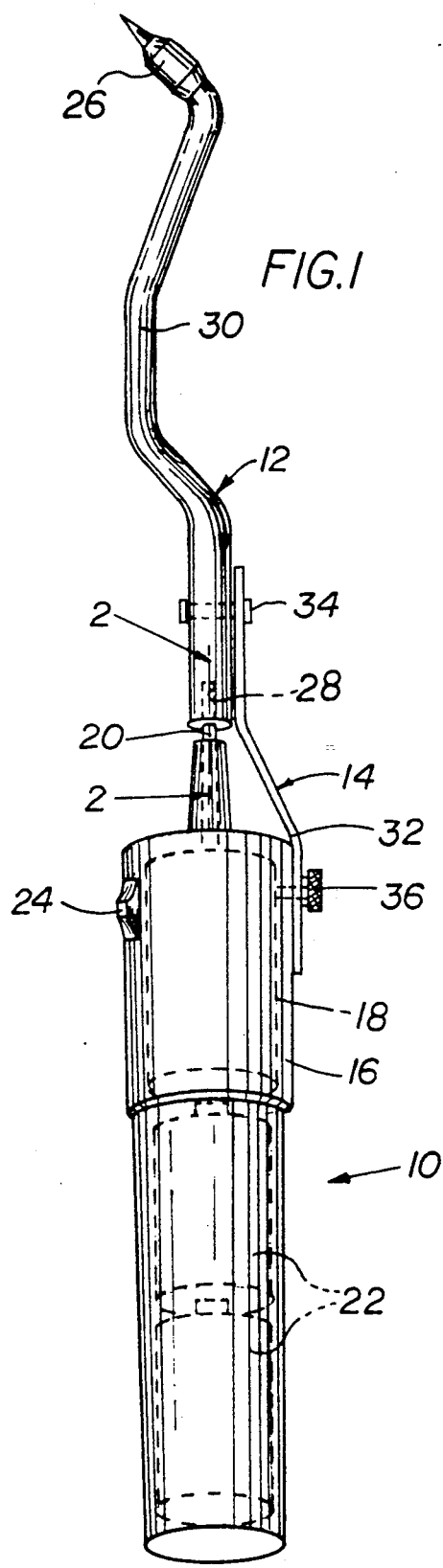
FIG. 1 is a representative prior art combination of a handle which houses a rechargeable battery source and to which there is attached a moveable wand with a distal tip end which moves.
Figure 2:
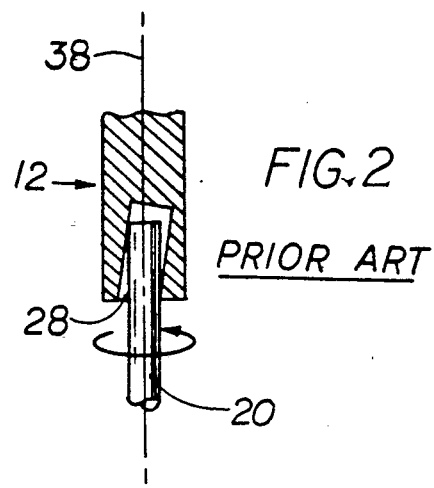
FIG. 2 illustrates the means for causing movement of the wand of FIG. 1.

For purposes of explanation, reference is made to U.S. Pat. No. 4,347,839 which is of a gum massaging device. That prior art discloses a power unit 10, a massage wand 12 connected to the power unit, and a resilient connection means 14 between the wand and the power unit. The power unit 10 includes a housing 16 containing a simple conventional motor 18 having an axially extending shaft 20 that rotates about its longitudinal axis upon operation of the motor. The motor is preferably electric and is powered by one or more batteries 22 which may be located in the base of the housing 16. An on/off switch 24 for the motor is also preferably included in a convenient location on the device so as to enable selective operation of the motor when the power unit is held in the hand. Suitable series electrical connections between the batteries, switch and motor are conventional and for simplicity were not described in the prior art patent and are not here described. The motor can be operated from an AC or DC source and may utilize DC batteries which are rechargeable from an AC source, all of which are conventional. Alternatively, a mechanical motor such as one utilizing wind-up springs may be employed to rotate the shaft 20. The wand 20 is an elongate member which may be pointed or shaped as shown. The other end or base of the wand has a socket 28 to mate with the end of the shaft 20, see FIG. 2. In a preferred embodiment, the central portion of the wand may be bent or curved as at 30 away from the axis of the wand at the base which serves to amplify the motion imparted from the base to the tip. Alternatively, the wand may be of relatively rigid but, nevertheless, bendable material, such as plastic or metal, so that its contour may be varied to reach different locations in use. The base of the wand 12 and the shaft 20 of the power unit 10 are substantially in axial alignment and maintains in alignment by flexible strap 32 in the embodiment shown. One end of the strap 32 is secured to the wand by a pin or rivet 34 while the other end may be adjustably secured by an adjustable screw 36 to the housing 16, with the strap preferably following the contour of the connected parts. While the strap serves to retain the wand in operative engagement with the shaft, it is also prevents rotation of the wand. Referring to FIG. 2, the socket 28 in the base of the wand is not in axial alignment with the normal longitudinal axis 38 of the shaft 20 and wand. That is, the socket 28 is somewhat larger in diameter than the diameter of the shaft and is angularly disposed relative to the longitudinal axis 38. Upon rotation of the shaft, together with the constraining influence of the strap 32, the wand is caused to generate in a reciprocating osciloatory motion. The resulting motion imparted to the wand is quite rapid and vibratory like and is ideally suited for adaption to a gum massage device.

It will be appreciated that while there has been shown and described a handle with rechargeable battery means housed therein and a wand connected thereto for movement of the distal end of the wand, that various types of prior art devices may be utilized.

Figure 3:
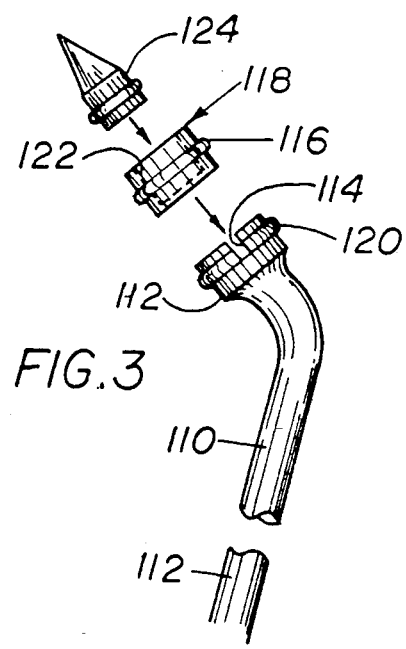
FIG. 3 is an exploded perspective view of the improvement of the present invention in one embodiment.

Referring now to FIG. 3, the improvement of the present invention will be described wherein there is the distal end zone 110 of a wand 112 shown partially broken away and wherein on the distal end, there is provided a female socket 112 which is adapted to yieldingly flex open by means of the slot 114 so that the bead 116 of a holder element 118 may be received and secured therein with the bead nesting in the annular groove 120. The holder includes a recess 122 which is sized to snugly receive a tip member 124.

Figure 4:
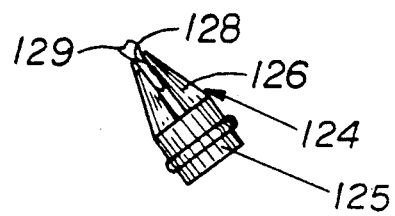
FIG. 4 is an alternative embodiment of the improvement.

The tip member may be as shown in FIG. 4 and include not only the base portion 125, but an extending, generally frusto-conical portion 126 which may have an axially extending groove notch or recess 128 in which medicament may be located as indicated by the dotted portion indicated by the numeral 129.

In use, the tip in FIG. 3 is inserted into the recess 122 and utilized for massaging the gums. As shown in FIG. 4, a supply of medicament may be inserted and held in to the notch or recess 128. The device when energized is useful for massaging and stimulating the gum tissues, especially the interdental papillae. The device may be used with other hygiene devices, such as a toothbrush and flossing. The electrically operated stimulator greatly enhances the quality and character of the general dental care and particularly of the gum tissue.

In summary, the device will be somewhat similar in construction to prior art devices, except that the tip, which is of absorbent yet durable material, will be movable, preferably in a vibrating manner, so that the tip in so moving will produce a massaging effect on the gum tissues. In general, the device will produce a stimulating effect upon the gum tissues and it may be utilized, in the embodiment shown in FIG. 4, to carry chemotherapeutic solutions to the gingival tissues. In any event, it is preferred that the tip be constructed of an absorbent yet firm material. Various conventional materials are available on the market which are relatively soft yet absorbent and may be utilized as the vibrating tip material. In the second embodiment, the vibrating tip actually physically carries a supply of medicament. The stimulating action of a device preferably includes a controlled vibratory motion and a side-to-side motion which serves to stimulate the marginal-cervical areas of the gum tissues. The absorbent material may be applied to the surface as an exterior element, but in any event, it serves, in either embodiment, to allow for the introduction of medicinal solutions to the sucular areas where initial gingivitis conditions take place or, in more advanced cases, where periodontitis conditions are located. In general, the device is composed of a electrically activated shaft or wand connected to a handle housing a motor and vibratory power source. The handle may, as is conventional, include rechargeable battery means for the batteries housed in the handle. The shaft or wand is preferably constructed of a hard flexible material which can be bent so that areas difficult to reach are more accessible. The tip, it is seen, carries by reason of its absorbent nature, a supply of medicament to enhance the effect of the device adding to the conventional vibratory and massaging type devices, the application of a medicament.

While this invention has been and described in what is considered to be a practical and preferred embodiment, it is recognized that departures may be made within the spirit and scope of this invention which is, therefore, not to be limited except as set forth in the claims hereinafter with the Doctrine of Equivalence.

What is claimed is:

1. A hand-held dental tool for massaging the gums of a user of the type which includes a wand with a distal tip zone and a handle connected to the wand including means to move the distal tip zone in a massaging motion, the improvement which comprises:

- a tip member formed of a substantially absorbent material adapted to carry a medicament for application to the gums during use of the tool, said tip member including a base portion and a conical end portion,
- a female socket disposed on the distal tip zone of the wand formed of a substantially yieldable, flexible material and including a slot opening therein,
- means to secure said tip member in a snug fitting relation within said female socket and including a holder element sized and configured to be received through said slot opening and into secured, fixed position within said female socket with a bead on an outer portion of said holder element being nested within a groove on an inner portion of said female socket, and
- said holder element including a recess formed therein being structured and configured to hold and maintain said base portion of said tip member in snug fitting relation therein.

2. The device as set forth in claim 1 wherein said conical end portion includes a bifurcating slit formed therein being structured and disposed for holding a charge of the medicament for application to the gums during use of the tool.

* * * * *